United States Patent [19]

Tanaka et al.

[11] Patent Number: 5,792,867
[45] Date of Patent: Aug. 11, 1998

[54] METHOD OF ALKYLATING OF TRIAZINE DERIVATIVES

[75] Inventors: Norio Tanaka, Chiba-ken; Masataka Hatanaka, Yamaguchi-ken; Makoto Ishikawa, Chiba-ken; Yasuo Fukue, Chiba-ken; Isao Hashiba, Chiba-ken; Yoshihisa Watanabe, Kyoto-hu, all of Japan

[73] Assignee: Nissan Chemical Industries, Ltd., Tokyo, Japan

[21] Appl. No.: 571,828

[22] PCT Filed: Jul. 20, 1994

[86] PCT No.: PCT/JP94/01190

§ 371 Date: Feb. 5, 1996

§ 102(e) Date: Feb. 5, 1996

[87] PCT Pub. No.: WO95/03287

PCT Pub. Date: Feb. 2, 1995

[30] Foreign Application Priority Data

Jul. 20, 1993 [JP] Japan ................. 5-178955
May 10, 1994 [JP] Japan ................. 6-96592

[51] Int. Cl.$^6$ ........................... C07D 251/54
[52] U.S. Cl. ........................... 544/196
[58] Field of Search ........................... 544/194, 196, 544/204, 200

[56] References Cited

U.S. PATENT DOCUMENTS

| | | | |
|---|---|---|---|
| 2,228,161 | 1/1941 | Zerweck et al. | 260/248 |
| 2,385,766 | 9/1945 | Thurston | 117/161 |
| 4,101,520 | 7/1978 | Boldizar | 528/248 |
| 4,293,692 | 10/1981 | Pai et al. | 544/196 |
| 4,722,806 | 2/1988 | Lai et al. | 252/403 |
| 5,155,271 | 10/1992 | Aeschlimann | 564/176 |

FOREIGN PATENT DOCUMENTS

A 3-215564 9/1991 Japan.

OTHER PUBLICATIONS

"S–Triazines and Derivatives" *The Chemistry of Heterocyclic Compounds*, Edwin M. Smolin et al., Interscience Publishers Inc., New York, NY, (1959) pp. 338–388.

Berichte the Deutschen Chemischen Gesellschaft, vol. 18, p. 2755 (1885).

Donald W. Kaiser et al., "Cyanuric Chloride Derivatives. II. Substituted Melamines," J. Amer. Chem. Soc., vol. 73, p. 2984, Jul., 1951.

*Primary Examiner*—Mukund J. Shah
*Assistant Examiner*—Deepak R. Rao
*Attorney, Agent, or Firm*—Oliff & Berridge, PLC

[57] ABSTRACT

A method for alkylation of at least one or more amino groups or mono-substituted amino groups, each on a carbon atom of a triazine ring of 1,3,5-triazine derivatives (melamine, melamine derivatives and various kinds of guanamine derivatives and the like), which includes reacting the 1,3,5-triazine derivatives having at least one or more amino groups or mono-substituted amino groups with alcohols in the presence of a catalyst of a metal of group VII and/or group VIII in the periodic table. The object of the invention is to provide a method for alkylation of 1,3,5-triazine derivatives, which includes alkylating amino groups or mono-substituted amino groups in carbon atoms of a 1,3,5-triazine ring, whereby substituted 1,3,5-triazine derivatives which are a group of useful compounds and which are widely used as intermediates of fine chemicals such as agricultural chemicals, medications, dye-stuffs, paints and the like, as resin materials and as flame-retardant materials can be easily produced in high yields.

17 Claims, No Drawings

METHOD OF ALKYLATING OF TRIAZINE DERIVATIVES

This application is a 371 of PCT/JP94/01190 filed on Jul. 20, 1994.

TECHNICAL FIELD

The present invention relates to a method for alkylation of 1,3,5-triazine derivatives having at least one or more amino groups or mono-substituted amino groups, which comprises reacting the 1,3,5-triazines having at least one or more amino groups or mono-substituted amino groups with alcohols in the presence of a catalyst of a metal of group VII and/or group VIII in the periodic table.

The substituted 1,3,5-triazine derivatives obtained by alkylation of the amino group(s) on the carbon atom(s) of the triazine ring of the 1,3,5-triazine derivatives in the present invention are a group of useful compounds which are widely used as intermediates of fine chemicals such as agricultural chemicals, medications, dyestuffs, paints and the like, as resin materials, among others, as aminoplasts-forming components, and as flame-retardant materials.

TECHNICAL BACKGROUND

As a method for producing substituted triazines, various methods have been known so far. Reported are, for example, a method in which a compound of formula (III)

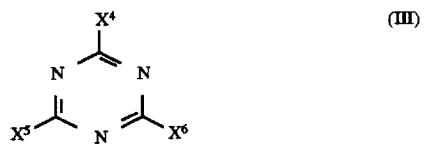

wherein $X^4$ and $X^5$ each represent an amino group, and $X^6$ represents an ethylamino group or a diethylamino group is produced by the reaction of 2-chloro-1,3,5-triazine with ethylamine (J. Amer. Chem. Soc., vol. 73, p. 2984, 1951), a method in which a compound of formula (III) wherein $X^4$, $X^5$ and $X^6$ each represent an ethylamino group is produced by the reaction of 2,4,6-trimethylthio-1,3,5-triazine with ethylamine (Chem. Ber., vol. 18, p. 2755, 1885), a method in which a compound of formula (III) wherein $X^4$ represents an amino group, $X^5$ represents an amino group or an octylamino group, and $X^6$ represents an octylamino group is produced by the reaction of 2,4,6-triamino-1,3,5-triazine with octylamine hydrochloride (U.S. Pat. No. 2,228,161, 1941), and a method in which a compound of formula (III) wherein $X^4$ represents a phenyl group, and $X^5$ and $X^6$ each represent a butylamino group is produced by the reaction of 2-phenyl-4,6-diamino-1,3,5-triazine with butylamine (U.S. Pat. No. 2,385,766, 1945). Further, substituted 2,4,6,-triamino-1,3,5-triazine derivatives produced from cyanuric chloride are used as a flame retardant of a thermoplastic polymer (Japanese Patent Application Laid-Open No. Hei 3-215564). Specific examples of the derivatives described in this Japanese Patent Application Laid-open No. Hei 3-215564 are as follows as a part thereof.

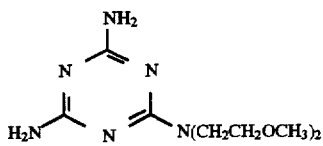

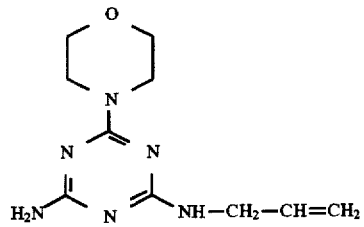

The method described in J. Amer. Chem. Soc., vol. 73, p. 2984, 1954 requires a condensation agent in an amount of more than a stoichiometrical amount in many cases and causes formation of by-products such as salts and the like which is often industrially problematic. The method described in Chem. Ber., vol. 18, p. 2755, 1885 causes formation of by-products such as sulfur compounds and the like which is often industrially problematic. The methods described in U.S. Pat. Nos. 2,228,161 (1941) and No. 2,385,766 (1945) require high temperatures in the reaction. Besides, the former method causes formation of by-product ammonium chloride.

Any of the above-mentioned methods conduct the substitution reaction with the leaving group by using substituted amines which are not said to be industrially inexpensive, and this is one of the reasons that substituted triazines cannot be supplied at low costs.

The present inventors have assiduously conducted investigations to solve the problems associated with the prior art, and have consequently found a novel method of alkylating 1,3,5-triazine derivatives in which alkyl group can be introduced into amino group or mono-substituted amino group on carbon atom of the 1,3,5-triazine ring using alcohols which are industrially inexpensive and only water is formed as a by-product. This finding has led to the completion of the present invention.

Further, since the substituted 1,3,5-triazine derivatives obtained by the method of the present invention notably inhibit the inter-molecular association inherent in aminotriazine, solubility in solvents is improved. This is explained by referring to melamine for example. After the completion of the reaction, unreacted melamine is mostly crystallized and precipitated in a solvent used in the reaction, and is separated through filtration or the like. Meanwhile, approximately the total amount of the reaction product is dissolved in the solvent. Accordingly, the method of the present invention is also excellent in terms of separation and purification of the reaction product.

It is an object of the present invention to provide a method for alkylation of 1,3,5-triazine derivatives, which comprises alkylating amino groups or mono-substituted amino groups on carbon atoms of a 1,3,5-triazine ring, whereby substituted 1,3,5-triazine derivatives which are a group of useful compounds and which are widely used as intermediates of fine chemicals such as agricultural chemicals, medications, dyestuffs, paints and the like, as resin materials and as flame-retardant materials can easily be produced in high yields.

DISCLOSURE OF THE INVENTION

That is, the present invention relates to a method for alkylation of at least one or more amino groups or mono-substituted amino groups on carbon atom of a triazine ring of 1,3,5-triazine derivatives, which comprises reacting the 1,3,5-triazine derivatives having at least one or more amino groups or mono-substituted amino groups with alcohols in the presence of a catalyst of a metal of group VII and/or group VIII in the periodic table.

Alkylating amino groups or mono-substituted amino groups in the present invention means that amino groups are converted into mono- or di-alkylamino groups or mono-substituted amino groups are converted into di-alkylamino groups which is further alkylated.

The present invention will be described in more detail below. The 1,3,5-triazine derivatives having at least one or more amino groups or mono-substituted amino groups, which are starting materials of the present invention, are represented by formula (I).

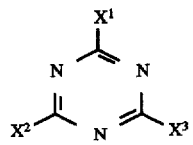

[wherein at least one of $X^1$, $X^2$ and $X^3$ independently represents $NHR^1$ {in which $R^1$ represents a hydrogen atom, a $C_{1-20}$ alkyl group (said alkyl group is optionally substituted with a trifluoromethyl group, a $C_{1-6}$ alkoxy group, a $C_{1-6}$ haloalkoxy group, a $C_{2-7}$ alkoxycarbonyl group, a phenyl group (said phenyl group is optionally substituted with a halogen atom, a $C_{1-6}$ alkyl group or a $C_{1-6}$ alkoxy group)) or a $C_{2-20}$ alkenyl group (said alkenyl group is optionally substituted with a trifluoromethyl group, a $C_{1-6}$ alkoxy group, a $C_{1-6}$ haloalkoxy group, a $C_{2-7}$ alkoxycarbonyl group or a phenyl group (said phenyl group is optionally substituted with a halogen atom, a $C_{1-6}$ alkyl group or a $C_{1-6}$ alkoxy group))}, and $X^1$, $X^2$ and $X^3$ which are not $NHR^1$ independently represent $NR^2R^3$ {in which $R^2$ and $R^3$ independently represent a $C_{1-20}$ alkyl group (said alkyl group is optionally substituted with a trifluoromethyl group, a $C_{1-6}$ alkoxy group, a $C_{1-6}$ haloalkoxy group, a $C_{2-7}$ alkoxycarbonyl group, a phenyl group (said phenyl group is optionally substituted with a halogen atom, a $C_{1-6}$ alkyl group or a $C_{1-6}$ alkoxy group)), a $C_{2-20}$ alkenyl group (said alkenyl group is optionally substituted with a trifluoromethyl group, a $C_{1-6}$ alkoxy group, a $C_{1-6}$ haloalkoxy group, a $C_{2-7}$ alkoxycarbonyl group or a phenyl group (said phenyl group is optionally substituted with a halogen atom, a $C_{1-6}$ alkyl group or a $C_{1-6}$ alkoxy group)), or $R^2$ and $R^3$ may together form —$(CH_2)_{2-5}$—, —$CH_2CH_2$—$(C_{1-3}$ alkyl group)N—$CH_2CH_2$— or —$CH_2CH_2$—O—$CH_2CH_2$— in which an alkylene chain is optionally substituted with one or two $C_3$ alkyl groups}, a $C_{1-3}$ alkyl group {said alkyl group is optionally substituted with a halogen atom, a nitro group, a cyano group, a $C_{1-6}$ alkoxy group, a carboxyl group, a $C_{2-7}$ alkoxycarbonyl group, a $C_{2-10}$ acyl group, a C2-10 acyloxy group, a $C_{2-7}$ dialkylamino group or an aryl group (said aryl group is optionally substituted with a halogen atom, a $C_{1-6}$ alkyl group or a $C_{1-6}$ alkoxy group)}, a $C_{2-20}$alkenyl group {said alkenyl group is optionally substituted with $C_{1-6}$ alkyl group a halogen atom, a nitro group, a cyano group, a $C_{1-6}$ alkoxy group, a carboxyl group, a $C_{2-7}$ alkoxycarbonyl group, a $C_{2-10}$ acyl group, a $C_{2-10}$ acyloxy group, a $C_{2-12}$ dialkylamino group or an aryl group (said aryl group is optionally substituted with a halogen atom, a $C_{1-6}$ alkyl group or a $C_{1-6}$ alkoxy group)}, a phenyl group {said phenyl group is optionally substituted with a $C_{1-6}$ alkyl group, a halogen atom, a nitro group, a cyano group, a $C_{1-6}$ alkoxy group, an aryloxy group, a carboxyl group, a $C_{2-7}$ alkoxycarbonyl group, a $C_{2-10}$ acyl group, a $C_{2-10}$ acyloxy group, a $C_{2-12}$ dialkylamino group or an aryl group (said aryl group is optionally substituted with a halogen atom, a $C_{1-6}$ alkyl group or a $C_{1-6}$ alkoxy group)}, a halogen atom, a $C_{1-10}$ alkoxy group {said alkoxy group is optionally substituted with a halogen atom, a nitro group, a cyano group, a $C_{1-6}$ alkoxy group, a carboxyl group, a $C_{2-7}$ alkoxycarbonyl group, a $C_{2-10}$ acyl group, a $C_{2-10}$ acyloxy group, a $C_{2-12}$ dialkylamino group or an aryl group (said aryl group is optionally substituted with a halogen atom, a $C_{1-6}$ alkyl group or a $C_{1-6}$ alkoxy group)}, or a $C_{2-10}$ alkylthio group {said alkylthio group is optionally substituted with a halogen atom, a nitro group, a cyano group, a $C_{1-6}$ alkoxy group, a carboxyl group, a $C_{2-7}$ alkoxycarbonyl group, a $C_{2-10}$ acyl group, a $C_{2-10}$ acyloxy group, a $C_{2-12}$ dialkylamino group, an aryl group (said aryl group is optionally substituted with a halogen atom, a $C_{1-6}$ alkyl group or a $C_{1-6}$ alkoxy group)}.

In the specification and claims of the present application, the expression "which is optionally substituted with a substituent . . . " means "which may be substituted with one or more of substituents which are the same or different and which are selected from substituents . . . ".

Preferable are 1,3,5-triazine derivatives of the formula (I) of the 1,3,5-triazine derivatives in which $R^1$ of $NHR^1$ represents a hydrogen atom, a $C_{1-20}$ alkyl group {said alkyl group is optionally substituted with a $C_{1-6}$ alkoxy group, a phenyl group (said phenyl group is optionally substituted with a halogen atom, a $C_{1-6}$ alkyl group or a $C_{1-6}$ alkoxy group)}, a $C_{2-20}$ alkenyl group {said alkenyl group is optionally substituted with a $C_{1-6}$ alkoxy group or a phenyl group (said phenyl group is optionally substituted with a halogen atom, a $C_{1-6}$ alkyl group or a $C_{1-6}$ alkoxy group)}, and $X^1$, $X^2$ and $X^3$ which are not $NHR^1$independently represent $NR^2R^3$ [in which $R^2$ and $R^3$ independently represent a $C_{1-20}$ alkyl group {said alkyl group is optionally substituted with a $C_{1-6}$ alkoxy group or a phenyl group (said phenyl group is optionally substituted with a halogen atom, a $C_{1-6}$ alkyl group or a $C_{1-6}$ alkoxy group)}, or a $C_{2-20}$ alkenyl group {said alkenyl group is optionally substituted with a $C_{1-6}$ alkoxy group or a phenyl group (said phenyl group is optionally substituted with a halogen atom, a $C_{1-6}$ alkyl group or a $C_{1-6}$ alkoxy group)}, or $R^2$ and $R^3$ may together form —$(CH_2)_{3-5}$—, —$CH_2CH_2$—$(C_{1-3}$ alkyl group)N—$CH_2CH_2$— or —$CH_2CH_2$—O—$CH_2CH_2$— in which an alkylene chain is desirably substituted with one or two $C_{1-3}$ alkyl groups), a $C_{1-20}$ alkyl group {said alkyl group is optionally substituted with a halogen atom, a $C_{1-6}$ alkoxy group or an aryl group (said aryl group is optionally substituted with a halogen atom, a $C_{1-6}$ alkyl group or a $C_{1-6}$ alkoxy group)}, a phenyl group (said phenyl group is optionally substituted with a $C_{1-6}$ alkyl group, a halogen atom or a $C_{1-6}$ alkoxy group), a halogen atom, or a $C_{1-10}$ alkoxy group {said alkoxy group is optionally substituted with a halogen atom, a $C_{1-6}$ alkoxy group, or an aryl group (said aryl group is optionally substituted with a halogen atom, a $C_{1-6}$ alkyl group or a $C_{1-6}$ alkoxy group)}].

More preferable triazine derivatives of the formula (I) are triazine derivatives of the formula (I) in which $R^1$ of $NHR^1$ represents a hydrogen atom or a $C_{1-20}$ alkyl group, and $X^1$, $X^2$ and $X^3$ which are not $NHR^1$ independently represent $NR^2R^3$ (in which $R^2$ and $R^3$ independently represent a $C_{1-20}$ alkyl group, or $R^2$ and $R^3$ may together form —$(CH_2)_{4-5}$—, —$CH_2CH_2$—$(C_{1-3}$ alkyl group)$N$—$CH_2CH_2$— or —$CH_2CH_2$—$O$—$CH_2CH_2$— in which an alkylene chain is optionally substituted with one or two $C_{1-3}$ alkyl groups), a $C_{2-20}$ alkyl group, a phenyl group, or a $C_{1-10}$ alkoxy group.

All of the 1,3,5-triazine derivatives having substituents which do not react under the reaction conditions of the present invention can be used as substrates of the reaction as mentioned above. Melamine derivatives and guanamine derivatives can be mentioned as industrially available intermediates (these are used mainly as modifier of thermosetting resins or crosslinking agents for baking paints, and a method of producing the same is detailed in "s-Triazines and Derivatives, The Chemistry of Heterocyclic Compounds, E. M. Smolin and L. Rapoport, Interscience Publishers Inc., New York 1959").

The alcohols which can be used in the present invention are alcohol derivatives represented by formula (II):

ROH  (II)

[wherein R represents a $C_{1-20}$ alkyl group {said alkyl group optionally substituted with a hydroxyl group, a trifluoromethyl group, a $C_{1-6}$ alkoxy group, a $C_{1-6}$ haloalkoxy group, a $C_{2-7}$ alkoxycarbonyl group or a phenyl group (said phenyl group is optionally substituted with a halogen atom, a $C_{1-6}$ akyl group or a $C_{1-6}$ alkoxy group)}, or a $C_{2-20}$ alkenyl group {(said alkenyl group is optionally substituted with a trifluoromethyl group, a $C_{1-6}$ alkoxy group, a $C_{1-6}$ haloalkoxy group, a $C_{2-7}$ alkoxycarbonyl group or a phenyl group (said phenyl group is optionally substituted with a halogen atom, a $C_{1-6}$ alkyl group or a $C_{1-6}$ alkoxy group)}]

Preferable are alcohol derivatives of formula (II) wherein R represents a $C_{1-20}$ alkyl group (said alkyl group is optionally substituted with a $C_{1-6}$ alkoxy group or a phenyl group) or a $C_{2-20}$ alkenyl group (said alkenyl group is optionally substituted with a $C_{1-6}$ alkoxy group or a phenyl group).

More preferable are alcohol derivatives of formula (II) wherein R represents a $C_{1-10}$ alkyl group (said alkyl group is optionally substituted with a $C_{1-6}$ alkoxy group or a phenyl group).

Of these alcohol derivatives, industrially available are alkanols such as methanol, ethanol, n-propanol, n-butanol, n-hexanol, n-octanol and 2-ethylhexanol; cellosolves such as methoxyethanol, ethoxyethanol and isopropoxyethanol; and substituted or unsubstituted benzyl alcohols.

A catalyst of a metal of group VII in the periodic table which is used in the present invention is a manganese catalyst and/or a rhenium catalyst. A catalyst of a metal of group VIII in the periodic table which is used in the present invention includes catalysts of metals such as iron, cobalt, nickel, ruthenium, rhodium, palladium, osmium, iridium, and platinum. For example, complex catalysts of the above-mentioned elements, these elements-carried catalysts or the like can be mentioned. Of these elements, the catalysts of the metals of group VIII in the periodic table, namely, nickel, ruthenium, rhodium, palladium, and platinum are preferable. The complex catalyst of ruthenium or rhodium is especially preferable.

The catalyst used in the present invention is illustrated more specifically below.

Examples of the iron catalyst include complex catalysts such as pentacarbonyliron, dodecacarbonyltriiron, dichlorobis(triphenylphosphine)iron, tetracarbonyl (triphenylphosphine)iron and tricarbonylbis (triphenylphosphine)iron.

Examples of the cobalt catalyst include complex catalysts such as octacarbonyldicobalt, dodecacarbonyltricobalt and chlorotris(triphenylphosphine)cobalt.

Examples of the nickel catalyst include catalysts such as nickel-carried silica, nickel-carried alumina, and nickel-carried carbon; complex catalysts such as dichlorobis (triphenylphosphine)nickel, tetrakis(triphenylphosphine) nickel and tetrakis(triphenylphosphite)nickel; nickel chloride; and nickel oxide.

Examples of the ruthenium catalyst include catalysts such as ruthenium-carried silica, ruthenium-carried alumina and ruthenium-carried carbon; complex catalysts such as pentacarbonylruthenium, dodecacarbonyltriruthenium, tetrahydridododecacarbonyltetraruthenium, dihydrido(dinitrogen)tris(triphenylphosphine)ruthenium, dicarbonyltris(triphenylphosphine)ruthenium, tetracarbonyl(trimethylphosphite)ruthenium, pentakis(trimethylphosphite)ruthenium, tris(acetylacetonato)ruthenium, diacetatodicarbonylbis(triphenylphosphine)ruthenium, dichlorobis(chlorotricarbonyl)ruthenium, carbonylchlorohydridotris(triphenylphosphine)ruthenium, tetrahydridotris(triphenylphosphine)ruthenium, acetatohydridotris(triphenylphosphine)ruthenium, dichlorobis(acetonitrile)bis(triphenylphosphine)ruthenium, ruthenocene, bis(pentamethylcyclopentadienyl)ruthenium, dichloro(pentamethylcyclopentadienyl)ruthenium, chloro(cyclopentadienyl)bis(triphenylphosphine)ruthenium, hydrido(cyclopentadienyl)bis(triphenylphosphine) ruthenium, chlorocarbonyl(cyclopentadienyl)ruthenium, hydrido(cyclopentadienyl)(1,5-cyclooctadiene)ruthenium, chloro(cyclopentadienyl)(1,5-cyclooctadiene)ruthenium, dihydridotetrakis(triphenylphosphine)ruthenium, cyclooctatriene(cyclooctadiene)ruthenium, chlorohydridotris(triphenylphosphine)ruthenium, tricarbonylbis(triphenylphosphine)ruthenium, tricarbonyl(cyclooctatetraene)ruthenium, tricarbonyl(1,5-cyclooctadiene)ruthenium and dichlorotris(triphenylphosphine)ruthenium; ruthenium chloride; and ruthenium oxide.

Of these ruthenium catalysts, preferable are catalysts such as ruthenium-carried silica, ruthenium-carried alumina and ruthenium-carried carbon; complex catalysts such as dodecacarbonyltriruthenium, carbonylchlorohydridotris(triphenylphosphine)ruthenium, tetrahydridotris(triphenylphosphine)ruthenium, dichlorobis(acetonitrile)bis(triphenylphosphine)ruthenium and dichlorotris(triphenylphosphine)ruthenium; ruthenium chloride and ruthenium oxide. More preferable ruthenium catalysts are complex catalysts such as dodecacarbonyltriruthenium, dichlorobis(acetonitrile)bis (triphenylphosphine)ruthenium, and dichlorotris (triphenylphosphine)ruthenium; and ruthenium chloride.

Examples of the palladium catalyst include catalysts such as palladium-carried silica, palladium-carried alumina and palladium-carried carbon; complex catalysts such as dichlorobis(triphenylphosphine)palladium,
dichlorobis(trimethylphosphine)palladium,
dichlorobis(tributylphosphine)palladium,
bis(tricyclohexylphosphine)palladium,
tetrakis(triethylphosphite)palladium,
bis(cycloocta-1,5-diene)palladium,
tetrakis(triphenylphosphine)palladium,
dicarbonylbis(triphenylphosphine)palladium,
carbonyltris(triphenylphosphine)palladium,
dichlorobis(benzonitrile)palladium and
dichloro(1,5-cyclooctadiene)palladium; palladium chloride; and palladium oxide.

Examples of the rhodium catalyst include catalysts such as rhodium-carried silica, rhodium-carried alumina, and rhodium-carried carbon; complex catalysts such as chlorotris(triphenylphosphine)rhodium,
hexadecacarbonylhexarhodium,
dodecacarbonyltetrarhodium,
dichlorotetracarbonylrhodium,
hydridotetracarbonylrhodium,
hydridocarbonyltris(triphenylphosphine)rhodium,
hydridotetrakis(triphenylphosphine)rhodium,
dichlorobis(cyclooctadiene)dirhodium,
dicarbonyl(pentamethylcyclopentadienyl)rhodium,
cyclopentadienylbis(triphenylphosphine)rhodium and
dichlorotetrakis(allyl)dirhodium; rhodium chloride; and
rhodium oxide. Of these, chlorotris(triphenylphosphine)-rhodium is preferable.

Examples of the platinum catalyst include catalysts such as platinum-carried silica, platinum-carried alumina, and platinum-carried carbon; complex catalysts such as
dichlorobis(triphenylphosphine)platinum,
dichlorobis(trimethylphosphine)platinum,
dichlorobis(tributylphosphine)platinum,
tetrakis(triphenylphosphine)platinum,
tetrakis(triphenylphosphite)platinum,
tris(triphenylphosphine)platinum,
dicarbonylbis(triphenylphosphine)platinum,
carbonyltris(triphenylphosphine)platinum,
cis-bis(benzonitrile)dichloroplatinum, and
bis(1,5-cyclooctadiene)platinum; platinum chloride; and platinum oxide.

The above-mentioned catalysts may be used either singly or in combination. The amount of the catalyst of group VII and/or group VIII in the periodic table is usually between 0.0001 and 20 mol %, preferably between 0.001 and 10 mol % based on the 1,3,5-triazine derivatives of formula (I).

A ligand can be added to the above-mentioned catalysts if necessary. Examples of the ligand include monodentate or multidentate tertiary phosphines such as trimethylphosphine,
triethylphosphine, tributylphosphine, triphenylphosphine,
tris(p-tolyl)phosphine, tris(2,6-dimethylphenyl)phosphine,
sodium diphenylphosphinobenzene-3-sulfonate,
bis(3-sulfonatophenyl)phosphinobenzene sodium salt,
1,2-bis(diphenylphosphino)ethane,
1,3-bis(diphenylphosphino)propane,
1,4-bis(diphenylphosphino)butane and
tris(3-sulfonatophenyl)phosphine sodium salt; phosphorous esters such as triethyl phosphite, tributyl phosphite, triphenyl phosphite and tris(2,6-dimethylphenyl) phosphite; phosphonium salts such as triphenylmethylphosphonium iodide,
triphenylmethylphosphonium bromide,
triphenylmethylphosphonium chloride,
triphenylallylphosphonium iodide, triphenylallylphosphonium
bromide, triphenylallylphosphonium chloride,
tetraphenylphosphonium iodide, tetraphenylphosphonium bromide, and tetraphenylphosphonium chloride; phosphate (phosphoric esters) such as triphenyl phosphate, trimethyl phosphate, triethyl phosphate, and triallyl phosphate; unsaturated hydrocarbons such as cyclooctadiene, and cyclopentadiene; nitrites such as benzonitrile, and acetonitrile; and acetylacetone.

Of these ligands, preferable are monodentate or multidentate tertiary phosphines such as trimethylphosphine, triethylphosphine, tributylphosphine, triphenylphosphine, tris(p-tolyl)phosphine, tris(2,6-dimethylphenyl)phosphine, sodium diphenylphosphinobenzene-3-sulfonate, bis(3-sulfonatophenyl)phosphinobenzene sodium salt, 1,2-bis(diphenylphosphino)ethane, 1,3-bis(diphenylphosphino)propane, 1,4-bis(diphenylphosphino)butane, and tris(3-sulfonatophenyl)phosphine sodium salt; unsaturated hydrocarbons such as cyclooctadiene, and cyclopentadiene; nitrites such as benzonitrile and acetonitrile; and acetylacetone.

Especially preferable are triphenylphosphine, sodium diphenylphosphinobenzene-3-sulfonate, bis(3-sulfonatophenyl)-phosphinobenzene sodium salt, and tris(3-sulfonatophenyl)-phosphine sodium salt.

The amount of the ligand is usually between 0.1 and 10,000 mol %, preferably between 10 and 5,000 mol % based on the catalyst of the metal of group VIII in the periodic table.

The reaction temperature is usually between approximately room temperature and 500° C., preferably between 50 and 300° C.

The reaction time varies depending on the reactivity of the 1,3,5-triazine derivatives of formula (I). It is, normally, between 1 and 100 hours, preferably between 2 and 50 hours.

Although the reaction proceeds in the absence of a solvent, a solvent can be used as required in view of operability and the like.

The solvent is not particularly limited so long as it is inert to the reaction. Examples of the solvent include ethers such as tetrahydrofuran, diethyl ether, diethylene glycol diethyl ether, and 1,4-dioxane; aromatic hydrocarbons such as benzene, toluene, xylene, and tetrahydronaphthalene; aliphatic hydrocarbons such as n-hexane, cyclohexane, n-octane, and n-decane; amides such as N,N-dimethylformamide, N,N-dimethylacetamide and N-methylpyrrolidone; and ureas such as 1,3-dimethylimidazolidinone, and N,N,N',N'-tetramethylurea. Excess alcohol derivatives represented by formula (II) may be used as a solvent.

Of these solvents, preferable are ethers such as tetrahydrofuran, diethyl ether, diethylene glycol diethyl ether, and 1,4-dioxane; aromatic hydrocarbons such as benzene, toluene, xylene, and tetrahydronaphthalene; aliphatic hydrocarbons such as n-hexane, cyclohexane, n-octane and n-decane; and excess alcohol derivatives of formula (II).

Especially preferable are ethers such as tetrahydrofuran, diethyl ether, diethylene glycol diethyl ether, and 1,4-dioxane; and excess alcohol derivatives of formula (II).

The reaction of the present invention can be carried out under an atmosphere of various gases which do not react with 1,3,5-triazine derivatives or alcohols under the present reaction conditions. For example, nitrogen, argon and helium are ordinarily used. Carbon dioxide and air are also available. For stabilizing the product and the catalyst, ammonia, hydrogen and carbon monoxide are also used. These gases may be used either singly or in combination.

A spontaneous pressure of a solvent or the like of a reaction system occurs during the reaction. A reaction pressure which is a total of the spontaneous pressure and the pressure of the gas atmosphere in the reaction can freely be selected within the range of between 1 and 500 kg/cm², preferably between 1 and 200 kg/cm².

After the completion of the reaction, unreacted triazines are removed through filtration or the like, and the solvent is then removed through distillation or the like as required, or a product is extracted into an organic solvent layer as a two-phase system of water and an organic solvent, and is then purified and isolated through recrystallization, distillation, separation using chromatography or the like.

The elements-carried catalysts are collected by filtration or the like. The organic metal complex catalyst is collected by the residue obtained after collecting the product through distillation, recrystallization or the like and removing the solvent. The catalyst with water-soluble ligand is collected in an aqueous layer as a water-soluble metal complex through extraction. Thus, the catalysts can be separated, collected and reused in various forms.

The substituted triazine derivatives obtained by the method for alkylation of amino groups on carbon atoms of the 1,3,5-triazine ring in the present invention are substituted 1,3,5-triazine derivatives represented by formula (III)

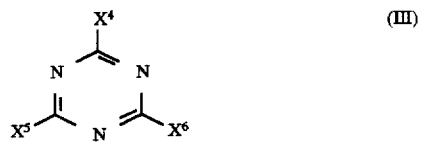

[wherein at least one of $X^4$, $X^5$ and $X^6$ independently represents $NR^4R^5$ {in which $R^4$ and $R^5$ independently represent a hydrogen atom (provided that a case where $R^4$ and $R^5$ of $X^4$, $X^5$ and $X^6$ are all hydrogen atoms is excluded), a $C_{1-20}$ alkyl group (said alkyl group is optionally substituted with a hydroxyl group, a trifluoromethyl group, a $C_{1-6}$ alkoxy group, a $C_{1-6}$ haloalkoxy group, a $C_{2-7}$ alkoxycarbonyl group, a phenyl group (said phenyl group is optionally substituted with a halogen atom, a $C_{1-6}$ alkyl group or a $C_{1-6}$ alkoxy group)), or a $C_{2-20}$ alkenyl group (said alkenyl group is optionally substituted with a trifluoromethyl group, a $C_{1-6}$ alkoxy group, a $C_{1-6}$ haloalkoxy group, a $C_{2-7}$ alkoxycarbonyl group or a phenyl group (said phenyl group is optionally substituted with a halogen atom, a $C_{1-6}$ alkyl group or a $C_{1-6}$ alkoxy group)) or $R^4$ and $R^5$ may together form —(CH$_2$)$_{2-5}$—, —CH$_2$CH$_2$—(C$_{1-3}$ alkyl group)N—CH$_2$CH$_2$— or —CH$_2$CH$_2$—O—CH$_2$CH$_2$— in which an alkylene chain is optionally substituted with one or two $C_3$ alkyl groups}, and $X^4$, $X^5$ and $X^6$ which are not $NR^4R^5$ independently represent a $C_{1-20}$ alkyl group {said alkyl group is optionally substituted with a halogen atom, a nitro group, a cyano group, a $C_{1-6}$ alkoxy group, a carboxyl group, a $C_{2-7}$ alkoxycarbonyl group, a $C_{2-10}$ acyl group, a $C_{2-10}$ acyloxy group, a $C_{2-12}$ dialkylamino group or an aryl group (said aryl group is optionally substituted with a halogen atom, a $C_{1-6}$ alkyl group or a $C_{1-6}$ alkoxy group)}, a $C_{2-20}$ alkenyl group {said alkenyl group is optionally substituted with a halogen atom, a nitro group, a cyano group, a $C_{1-6}$ alkoxy group, a carboxyl group, a $C_{2-7}$ alkoxycarbonyl group, a $C_{2-10}$ acyl group, a $C_{2-10}$ acyloxy group, a $C_{2-12}$ dialkylamino group or an aryl group (said aryl group is optionally substituted with a halogen atom, a $C_{1-6}$ alkyl group or a $C_{1-6}$ alkoxy group)}, a phenyl group {said phenyl group is optionally substituted with a $C_{1-6}$ alkyl group, a halogen atom, a nitro group, a cyano group, a $C_{1-6}$ alkoxy group, an aryloxy group, a carboxyl group, a $C_{2-7}$ alkoxycarbonyl group, a $C_{2-10}$ acyl group, a $C_{2-10}$ acyloxy group, a $C_{2-12}$ dialkylamino group or an aryl group (said aryl group is optionally substituted with a halogen atom, a $C_{1-6}$ alkyl group or a $C_{1-6}$ alkoxy group)}, a halogen atom, a $C_{1-10}$ alkoxy group {said alkoxy group is optionally substituted with a halogen atom, a nitro group, a cyano group, a $C_{1-6}$ alkoxy group, a carboxyl group, a $C_{2-7}$ alkoxycarbonyl group, a $C_{2-10}$ acyl group, a $C_{2-10}$ acyloxy group, a $C_{2-12}$ dialkylamino group or an aryl group (said aryl group is optionally substituted with a halogen atom, a $C_{1-6}$ alkyl group or a $C_{1-6}$ alkoxy group)}, or a $C_{1-10}$ alkylthio group {said alkylthio group is optionally substituted with a halogen atom, a nitro group, a cyano group, a $C_{1-6}$ alkoxy group, a carboxyl group, a $C_{2-7}$ alkoxycarbonyl group, a $C_{2-10}$ acyl group, a $C_{2-10}$ acyloxy group, a $C_{2-12}$ dialkylamino group or an aryl group (said aryl group is optionally substituted with a halogen atom, a $C_{1-6}$ alkyl group or a $C_{1-6}$ alkoxy group)}].

Preferable are substituted 1,3,5-triazine derivatives of formula (III) are substituted 1,3,5-trizaine derivatives in which $R^4$ and $R^5$ of $NR^4R^5$ independently represent a hydrogen atom (provided that a case where $R^4$ and $R^5$ of $X^4$, $X^5$ and $X^6$ are all hydrogen atoms is excluded), a $C_{1-20}$ alkyl group {(said alkyl group is optionally substituted with a $C_{1-6}$ alkoxy group or a phenyl group (said phenyl group is optionally substituted with a halogen atom, a $C_{1-6}$ alkyl group or a $C_{1-6}$ alkoxy group)}, or a $C_{2-20}$ alkenyl group {said alkenyl group is optionally substituted with a $C_{1-6}$ alkoxy group, a phenyl group (said phenyl group is optionally substituted with a halogen atom, a $C_{1-6}$ alkyl group or a $C_{1-6}$ alkoxy group)}, or $R^4$ and $R^5$ may together form —(CH$_2$)$_{3-5}$—, —CH$_2$CH$_2$—(C$_3$ alkyl group)N—CH$_2$CH$_2$— or —CH$_2$CH$_2$—O—CH$_2$CH$_2$— in which an alkylene chain is optionally substituted with one or two $C_{1-3}$ alkyl groups, and X4, $X^5$ and $X^6$ which are not $NR^4R^5$ independently represent a $C_{1-20}$ alkyl group {said alkyl group is optionally substituted with a halogen atom, a $C_{1-6}$ alkoxy group or an aryl group (said aryl group is optionally substituted with a halogen atom, a $C_{1-6}$ alkyl group or a $C_{1-6}$ alkoxy group)}, a phenyl group (said phenyl group is optionally substituted with a $C_{1-6}$ alkyl group, a halogen atom or a $C_{1-6}$ alkoxy group), a halogen atom or a $C_{1-10}$ alkoxy group {said alkoxy group is optionally substituted with a halogen atom, a $C_{1-6}$ alkoxy group or an aryl group (said aryl group is optionally substituted with a halogen atom, a $C_{1-6}$ alkyl group or a $C_{1-6}$ alkoxy group)}.

More preferable substituted 1,3,5-triazine derivatives of formula (III) are substituted 1,3,5-triazine derivatives of the formula (III) wherein $R^4$ and $R^5$ of $NR^4R^5$ independently represents a hydrogen atom (provided that a case where $R^4$ and $R^5$ of $X^4$, $X^5$ and $X^6$ are all hydrogen atoms is excluded) or a $C_{1-20}$ alkyl group, or $R^4$ and $R^5$ may together form $-(CH_2)_{4-5}-$, $-CH_2CH_2-(C_3$ alkyl group)N$-$CH$_2$CH$_2-$ or $-CH_2CH_2-O-CH_2CH_2-$ in which an alkylene chain is desirably substituted with one or two $C_3$ alkyl groups, and $X^4$, $X^5$ and $X^6$ which are not $NR^4R^5$ independently represent a $C_{1-20}$ alkyl group, a phenyl group or a $C_{1-10}$ alkoxy group.

As stated above, various compounds are available as starting 1,3,5-triazine derivatives and alcohols in the process of the present invention. The 1,3,5-triazine derivatives having various substituents can be obtained from combinations of starting 1,3,5-triazine derivatives and alcohols by the method of the present invention.

As mentioned above, typical starting materials of the present invention are 1,3,5-triazine derivatives, such as melamine, melamine derivatives and guanamine derivatives, as well as alcohols such as alkanols, cellosolves and benzyl alcohols. Typical products are obtained by the combinations of these starting materials. Further, for example, substituted triazine derivatives obtained by alkylation of melamine by the present invention can be used as starting 1,3,5-triazine derivatives of the present invention if an amino group is present on a carbon atom of a triazine ring.

The starting materials which can be applied to the reaction of the present invention are not limited by the costs of the starting materials and ease of obtainment thereof. However, the range of the reaction in the present invention is more clarified by illustrating specific examples of the substituents of the starting materials and the products.

Specific examples of NHR$^1$, NR$^2$R$^3$ and NR$^4$R$^5$ among the substituents indicated by $X^1$, $X^2$ and $X^3$ of formula (I) representing the starting materials and by $X^4$, $X^5$ and $X^6$ of formula (III) representing the products include amino (melamine when $X^1$, $X^2$ and $X^3$ are amino groups), methylamino, ethylamino, isopropylamino, n-butylamino, i-butylamino, secbutylamino, tert-butylamino, cyclohexylamino, cyclohexylmethylamino, n-octylamino, dimethylamino, diethylamino, diisopropylamino, di-n-butylamino, di-i-butylamino, di-secbutylamino, methyl-tert-butylamino, methylcyclohexylamino, cyclohexylmethylamino, di-n-octylamino, dicyclohexylmethylamino, hydroxyethylamino, 4-hydroxybutylamino, 5-hydroxypentylamino, trifluoroethylamino, 2-trifluoropropylamino, 2-ethoxyethylamino, 3-methoxypropylamino, 2-pentyloxyethylamino, 3-cyclohexyloxypropylamino, 2-chloroethoxyethylamino, 5-monofluoropentyloxypentylamino, 2-methoxycarbonylethylamino, 2-ethoxycarbonylethylamino, tert-butoxycarbonylethylamino, 2-cyclohexyloxycarbonylethylamino, methylphenylamino, benzylamino, dibenzylamino, N-benzyl-N'-methylamino, 2-phenylethylamino, 3-(4-chlorophenyl)-propylamino, 2-(4-cyclohexylphenyl)-ethylamino, 2-(3-fluorophenyl)-pentylamino, 4-methoxybenzylamino, 2-chloro-4-fluorobenzylamino, 3,5-dimethylbenzylamino, 4-cyclopentyloxybenzylamino, 2-(2-chloro-4-fluoro-5-isopropylphenyl)-propylamino, allylamino, methallylamino, 3-cyclopentenylamino, 3-cyclohexenylamino, 3-(6-trifluoromethyl)-cyclohexenylamino, diallylamino, dimethallylamino, 3-(1-methoxy)-allyl, crotylamino, chloromethoxyethylamino, ethoxycarbonylallylamino, cinnamylamino, 4-chlorocinnamylamino, N-(4-methylcinnamyl)-N'-methylamino and 4-methoxycinnamylamino groups.

Specific examples of the group formed by binding of $R^2$ and $R^3$ of NR$^2$R$^3$ or by binding of $R^4$ and $R^5$ of NR$^4$R$^5$ include aziridino, pyrrolidino, piperidino, N-methylpiperazino and morpholino groups. Of these, pyrrolidino, piperidino, N-methylpiperazino and morpholino groups are preferable.

Specific examples of the optionally substituted $C_{1-20}$ alkyl groups include methyl, ethyl, n-propyl, n-butyl, i-butyl, sec-butyl, n-amyl, i-amyl, hexyl, cyclohexyl, cyclohexylmethyl, heptyl, octyl, 2-ethylhexyl, nonyl, decyl, hexadecyl, octadecyl, trifluoromethyl, 3-chloropropyl, cyanoethyl, 2-trifluoromethylethyl, nitroethyl, nitropropyl, methoxmethyl, methoxyethyl, ethoxymethyl, cyclohexylmethoxyethyl, 2-carboxyethyl, 3-carboxypropyl, methoxycarbonylmethyl, methoxycarbonylethyl, tert-butoxycarbonylmethyl, cyclohexyloxycarbonylethyl, 2-propanoylethyl, benzoylmethyl, 2,4,6-trimethylphenylbenzoylmethyl, acetyloxymethyl, benzoyloxymethyl, 3-(tert-butylcarbonyloxy)-propyl, dimethylaminomethyl, diethylaminomethyl, diisopropylaminomethyl, di-n-butylaminomethyl, di-i-butylaminomethyl, di-sec-butylaminomethyl, methyl-tert-butylaminomethyl, methylcyclohexylaminomethyl, cyclohexylmethylaminomethyl, benzyl, 4-methylbenzyl, 4-methoxybenzyl, 2-chloro-4-fluorobenzyl, 3,5-dimethylbenzyl and 4-cyclopentyloxybenzyl groups.

Specific examples of the optionally substituted $C_{2-20}$ alkenyl groups include vinyl, isopropenyl, 1-butenyl, 3-hexenyl, allyl, methallyl, crotyl, 2-chloroallyl, 2-cyanovinyl, methoxyvinyl, ethoxyvinyl, cyclohexylvinyl, 4-nitro-2-butenyl, 2-carboxylvinyl, ethoxycarbonylvinyl, tert-butoxycarbonylvinyl, acetylvinyl, acetylallyl, 3-benzoylallyl, acetyloxyvinyl, cyclohexanoyloxyvinyl, dimethylaminovinyl, 4-diethylaminobutenyl, dicyclohexylaminovinyl, cinnamyl, 4-chlorocinnamyl, 3,5-dimethoxycinnamyl, 2,4,6-trimethylcinnamyl, styryl, 2,4-dichlorostyryl, 6-dodecen-1-yl and 1,2-diphenylvinyl groups.

Specific examples of the optionally substituted phenyl group include phenyl, p-toluyl, m-toluyl, o-toluyl, 3,5-dimethylphenyl, 4-cyclohexylphenyl, 2,4,6-trimethylphenyl, p-nitrophenyl, 2-methyl-4-nitrophenyl, 2-chloro phenyl, 2,4-dichlorophenyl, 2-fluoro-4-chlorophenyl, p-cyanophenyl, 3,5-dimethoxyphenyl, 4-cyclopentyloxyphenyl, m-phenoxyphenyl, 4-(2-naphthyloxy)-phenyl, 4-carboxy phenyl, 4-methoxycarbonylphenyl, 3-cyclohexyloxycarbonylp hen yl, 2-acetylphenyl, 4-octanoyl phenyl, 4-acetyloxyphenyl, 3-cyclohexylcarbonyloxyphenyl, 2-dimethylaminophenyl, 4-diethylaminophenyl, 4-diisopropylaminoph enyl, 3-di-n-butylaminophe nyl, 3-di-i-butylaminophenyl, 2-di-sec-butylaminophenyl, 4-methyl-tertbutylaminophenyl, 4-methylcyclohexylaminophenyl, 4-cyclohexylmethylaminophenyl, 4-biphenyl, 4-(2-naphthyl)-phenyl, 4-(4-chlorophenyl)-phenyl and 4-(5-(1-methyl-3-chloropyrazolo)-yl )-phenyl groups.

Specific examples of the halogen atom include fluorine, chlorine, bromine and iodine atoms.

Specific examples of the optionally substituted $C_{1-10}$ alkoxy group include methoxy, ethoxy, n-propyloxy, i-propyloxy, n-butyloxy, i-butyloxy, sec-butyloxy, tertbutyloxy, n-amyloxy, i-amyloxy, hexyloxy, cyclohexyloxy, cyclohexylmethyloxy, heptyloxy, octyloxy, 2-ethylhexyloxy, nonyloxy, decyloxy, hexadecyloxy, octadecyloxy, trifluoromethyloxy, 3-cyloropropyloxy, cyanoethyloxy, 2-trifluoromethylethyloxy, nitroethyloxy, nitropropyloxy, methoxymethyloxy, methoxyethyloxy, ethoxymethyloxy, cyclohexylmethoxyethyloxy, 2-carboxyethyloxy, 3-carboxypropyloxy, methoxycarbonylmethyloxy, methoxycarbonylethyloxy, tert-butoxycarbonylmethyloxy, cyclohexyloxycarbonylethyloxy, 2-propanoylethyloxy, benzoylmethyloxy, 2,4,6-trimethylphenylbenzoylmethyloxy, acetyloxymethyloxy, benzoyloxymethyloxy, 3-(tert-butylcarbonyloxy)-propyloxy, dimethylaminomethyloxy, diethylaminomethyloxy, diisopropylaminomethyloxy, di-n-butylaminomethyloxy, di-i-butylaminomethyloxy, di-sec-butylaminomethyloxy, methyl-tert-butylaminomethyloxy, methylcyclohexylaminomethyloxy, cyclohexylmethylaminomethyloxy, benzyloxy, 4-methylbenzyloxy, 4-methoxybenzyloxy, 2-chloro-4-fluorobenzyloxy, 3,5-dimethylbenzyloxy and 4-cyclopentyloxybenzyloxy groups.

Specific examples of the optionally substituted $C_{1-10}$ alkylthio group include methylthio, ethylthio, n-propylthio, i-propylthio, n-butylthio, i-butylthio, sec-butylthio, tert-butylthio, n-amylthio, i-amylthio, hexylthio, cyclohexylthio, cyclohexylmethylthio, heptylthio, octylthio, 2-ethylhexylthio, nonylthio, decylthio, hexadecylthio, octadecylthio, trifluoromethylthio, 3-chloropropylthio, cyanoethylthio, 2-trifluoromethylethylthio, nitroethylthio, nitropropylthio, methoxymethylthio, methoxyethylthio, ethoxymethylthio, cyclohexylmethoxyethylthio, 2-carboxyethylthio, 3-carboxypropylthio, methoxycarbonylmethylthio, methoxycarbonylethylthio, tert-butoxycarbonylmethylthio, cyclohexyloxycarbonylethylthio, 2-propanoylethylthio, benzoylmethylthio, 2,4,6-trimethylphenylbenzoylmethylthio, acetyloxymethylthio, benzoyloxymethylthio, 3-(tert-butylcarbonyloxy)-propylthio, dimethylaminomethylthio, diethylaminomethylthio, diisopropylaminomethylthio, di-n-butylaminomethylthio, di-i-butylaminomethylthio, di-sec-butylaminomethylthio, methyl-tert-butylaminomethylthio, methylcyclohexylaminomethylthio, cyclohexylmethylaminomethylthio, benzylthio, 4-methylbenzylthio, 4-methoxybenzylthio, 2-chloro4-fluorobenzylthio, 3,5-dimethylbenzylthio and 4-cyclopentyloxybenzylthio groups.

The alcohols which are subjected to the reaction of the present invention as another starting material can be commercially available alcohols. Specific examples of the substituent indicated by R include methyl, ethyl, n-propyl, n-butyl, i-butyl, sec-butyl, n-amyl, i-amyl, hexyl, cyclohexyl, cyclohexylmethyl, heptyl, octyl, 2-ethylhexyl, nonyl, decyl, hexadecyl, octadecyl, trifluoroethyl, 3-chloropropyl, cyanoethyl, 2-trifluoromethylethyl, nitroethyl, nitropropyl, methoxymethyl, methoxyethyl, ethoxymethyl, cyclohexylmethoxyethyl, 2-carboxyethyl, 3-carboxypropyl, methoxycarbonylmethyl, methoxycarbonylethyl, tert-butoxycarbonylmethyl, cyclohexyloxycarbonylethyl, 2-propanoylethyl, benzoylmethyl, 2,4,6-trimethylphenylbenzoylmethyl, acetyloxymethyl, benzoyloxymethyl, 3-(tert-butylcarbonyloxy)-propyl, dimethylaminomethyl, diethylaminomethyl, diisopropylaminomethyl, di-n-butylaminomethyl, di-i-butylaminomethyl, di-sec-butylaminomethyl, methyl-tert-butylaminomethyl, methylcyclohexylaminomethyl, cyclohexylmethylaminomethyl, benzyl, 4-methylbenzyl, 4-methoxybenzyl, 2-chloro-4-fluorobenzyl, 3,5-dimethylbenzyl, 4-chloropentyloxybenzyl, allyl, homoallyl, methallyl, 3-cyclopentenyl, 3-cyclohexenyl, 3-(6-trifluoromethyl)-cyclohexenyl, 3-(1-methoxy)-allyl, crotylamino, cinnamyl, 4-methylcinnamyl, 4-chlorocinnamyl, 4-ethoxycinnamyl and 2,4,6-trimethylcinnamyl groups.

These examples of the substituents are typical ones, and the substituents of the present invention are not limited thereto.

In the treatment after the completion of the reaction, unreacted triazines are crystallized and removed by filtration or the like, after which the solvent is removed by distillation or the like as required. Or the product is extracted as a two-phase system of water and an organic solvent, and the reaction product is then purified and isolated by recrystallization, distillation, separation using chromatography or the like.

The element-carried catalyst is collected by filtration or the like. The organic metal complex catalyst is collected from the residue obtained after collecting the product and removing the solvent through distillation, recrystallization or the like. The catalyst with water-soluble ligand is collected in an aqueous layer as a water-soluble metal complex through extraction. Thus, the catalysts can be separated, collected and reused in various forms.

BEST MODE OF CARRYING OUT THE INVENTION

The present invention will be illustrated more specifically by referring to the following Examples. However, the present invention is not limited thereto.

In Examples 1 to 5, the composition of the reaction product was analyzed in the form of a mixture as such through FD-MASS spectrum (JMS-SX102 model manufactured by JEOL, Ltd.), and the reaction selectivity thereof was found from the peak intensity and the relative area ratio of high-performance liquid chromatography (L-6000 series made by Hitachi Ltd.).

In Example 6 and those following, a calibration curve was made using an internal standard substance and pure triazine derivatives which were formed separately as a specimen, and the concentrations of the components in the reaction system were determined under the following conditions.

The conditions for analysis of high-performance liquid chromatography (HPLC) are as follows.

Method of determing an amount of starting triazine:

Eluent: $CH_3CN/H_2O=1/1$ (v/v)

Detection method: UV 240 nm

Column: Inertsil Ph manufactured by GL Science,
150 mm×4.6 mm ø

Flow rate: 1.0 ml/min

Temperature: 40° C.

Internal standard substance: di-n-butyl phthalate (Method of determining amounts of a product and a part of a starting material alkylaminotriazines)):

Eluant: $CH_3CN/H_2O=40/60$ (v/v),
15 minutes later, $CH_3CN/H_2O=100/0$ (v/v), retained for 15 minutes (gradient system)

Detection method: UV 230 nm

Column: Inertsil C8 manufactured by GL Science,
150 mm×4.6 mm ø

Flow rate: 1.0 ml/min
Temperature: 35° C.
Internal standard substance: di(2-ethylhexyl)phthalate

EXAMPLE 1

Into a 20 mL glass-lined stainless steel autoclave with a magnetic rotor, 0.192 g (0.20 mmol) of dichlorotris (triphenylphosphine)ruthenium, 2.52 g (20.0 mmols) of melamine and ethanol (10.0 milliliters) were charged. The mixture was reacted at 180° C. under argon atmosphere (initial atmospheric pressure, 1 atm.) for 20 hours.

After the completion of the reaction, the reaction product was analyzed by HPLC and mass analysis (FD-MASS). As a result, the conversion ratio of the starting material was 50%, and the following products were obtained with the following selectivities.

2-ethylamino-4,6-diamino-1,3,5-triazine 20%

2,4-bis(ethylamino)-6-amino-1,3,5-triazine 24%

2,4,6-tris(ethylamino)-1,3,5-triazine 21%

2-diethylamino-4,6-bis(ethylamino)-1,3,5-triazine 8.2%

2-melamino-4-ethylamino-6-amino-1,3,5-triazine 10.9%

EXAMPLE 2

Into a 20 mL glass-lined stainless steel autoclave with a magnetic rotor, 0.096 g (0.10 mmols) of dichlorotris (triphenylphosphine)ruthenium, 1.26 g (10.0 mmols) of melamine and benzyl alcohol (10.0 milliliters) were charged. The mixture was reacted at 180° C. under argon atmosphere (initial atmospheric pressure, 1 atm) for 20 hours.

After the completion of the reaction, the reaction product was analyzed by HPLC and mass analysis (FD-MASS). As a result, the conversion ratio of the starting material was 43%, and the following products were obtained with the following selectivites.

2-benzylamino-4,6-diamino-1,3,5-triazine 20.5%

2,4-bis(benzylamino)-6-amino-1,3,5-triazine 29.1%

2,4,6-tris(benzylamino)-1,3,5-triazine 21.7%

2-dibenzylamino-4,6-bis(benzylamino)-1,3,5-triazine 2.0%

EXAMPLE 3

Into a 20 mL glass-lined stainless steel autoclave with a magnetic rotor, 0.096 g (0.10 mmol) of dichlorotris (triphenylphosphine)ruthenium, 1.26 g (10.0 mmols) of melamine and 1-butanol (10.0 milliliters) were charged. The mixture was reacted at 180° C. under argon atmosphere (initial atmospheric pressure, 1 atm.) for 20 hours.

After the completion of the reaction, the reaction product was analyzed through HPLC and mass analysis (FD-MASS). As a result, the conversion ratio of the starting material was 73%, and the following products were obtained with the following selectivities.

2-n-butylamino-4,6-diamino-1,3,5-triazine 12.9%

2,4-bis(n-butylamino)-6-amino-1,3,5-triazine 21%

2,4,6-tris(n-butylamino)-1,3,5-triazine 28.6%

2-di-n-butylamino-4,6-bis(n-butylamino)-1,3,5-triazine 13.7%

2,4-bis(di-n-butylamino)-6-n-butylamino-1,3,5-triazine 4.0%

EXAMPLE 4

Into a 20 mL glass-lined stainless steel autoclave with a magnetic rotor, 0.096 g (0.10 mmol) of dichlorotris (triphenylphosphine)ruthenium, 1.26 g (10.0 mmols) of melamine and 1.08 g (10.0 mmols) of benzyl alcohol were charged. Ten milliters of tetrahydronaphthalene were added thereto as a solvent, and the mixture was reacted at 180° C. under argon atmosphere (initial atmospheric pressure, 1 atm.) for 20 hours.

After the completion of the reaction, the reaction product was analyzed by HPLC and mass analysis (FD-MASS). As a result, the conversion ratio of the starting material was 75%, and the following products were obtained with the following selectivities.

2-benzylamino-4,6-diamino-1,3,5-triazine 16.7%

2,4-bis(benzylamino)-6-amino-1,3,5-triazine 20.7%

2,4,6-tris(benzylamino)-1,3,5-triazine 12.6%

EXAMPLE 5

Into a 20 mL glass-lined stainless autoclave with a magnetic rotor, 0.093 g (0.10 mmols) of chlorotris (triphenylphosphine)rhodium, 1.26 g (10.0 mmols) of melamine and 1-butanol (10.0 milliliters) were charged. The mixture was reacted at 180° C. under argon atmosphere (initial atmospheric pressure, 1 atm.) for 20 hours.

After the completion of the reaction, the reaction product was analyzed by HPLC and mass analysis (FD-MASS). As a result, the conversion ratio of the starting material was 5%, and the following products were obtained with the following selectivities.

2-n-butylamino-4,6-diamino-1,3,5-triazine 20.9%

2,4-bis(n-butylamino)-6-amino-1,3,5-triazine 25%

2,4,6-tris(n-butylamino)-1,3,5-triazine 25.2%

2-di-n-butylamino-4,6-bis(n-butylamino)-1,3,5-triazine 3.7%

EXAMPLE 6

Into a 100-mL stainless steel autoclave, 5.04 g (40.0 mmols) of melamine, 52.0 mg (0.2 mmols) of ruthenium trichloride hydrate, 364.0 mg (1 mmol) of sodium diphenylphosphinobenzene-3-sulfonate and 30 mL of 1-butanol were charged under a nitrogen atmosphere. The reaction mixture was heated and reacted at 250° C. and under a nitrogen atmosphere (initial pressure was 30 kg/cm$^2$) for 10 hours.

After the completion of the reaction, the resulting crude reaction product was analyzed by HPLC under the above-mention first method. As a result, the conversion ratio of the starting melamine was 95%. Further, the crude reaction product was analyzed by HPLC under the above-mentioned first method. Consequently, the following products were obtained in the following yields (based on the starting melamine).

2-n-butylamino-4,6-diamino-1,3,5-triazine 16.5%

2,4-bis(n-butylamino)-6-amino-1,3,5-triazine 35.0%

2,4,6-tris(n-butylamino)-1,3,5-triazine 23.6%

2-di-n-butylamino-4,6-bis(n-butylamino)-1,3,5-triazine 15.0%

After 1-butanol and water were distilled off from the reaction mixture, toluene was added to the residue. The separated toluene solution by filtration was analyzed by HPLC. As a result, a small amount of 2-n-butylamino-4,6-diamino1,3,5-triazine and approximately a total production amount of 2,4-bis(n-butylamino)-6-amino-1,3,5-triazine, 2,4,6-tris-(n-butylamino)-1,3,5-triazine and 2-di-n-butylamino-4,6-bis-(n-butylamino)-1,3,5-triazine were extracted in toluene, respectively.

Further, the insoluble matter was suspended in water, and the soluble portion was extracted and analyzed. Consequently, 98.0% of the catalyst component and a trace amount of melamine were recovered.

EXAMPLE 7

Into a 100-mL stainless steel autoclave, 5.04 g (40.0 mmols) of melamine, 79.7 mg (0.2 mmol) of tris (acetylacetonato)ruthenium, 262.0 mg (1 mmol) of triphenylphosphine and 30 milliliters of 1-butanol were charged under a nitrogen atomosphere. The reaction mixture was heated and reacted at 230° C. under a nitrogen atmosphere (initial pressure was 5 kg/cm$^2$) for 6 hours.

After the completion of the reaction, the resulting crude reaction product was analyzed by HPLC under the above-mentioned first method. As a result, the conversion ratio of the starting melamine was 79.0%. Further, the crude reaction product was analyzed by HPLC under the above-mentioned first method. Consequently, the following products were obtained in the following yields (based on the starting melamine).

2-n-butylamino-4,6-diamino-1,3,5-triazine 18.5%

2,4-bis(n-butylamino)-6-amino-1,3,5-triazine 21.5%

2,4,6-tris(n-butylamino)-1,3,5-triazine 15.3%

2-di-n-butylamino-4,6-bis(n-butylamino)-1,3,5-triazine 8.7%

EXAMPLE 8

Into a 100-mL stainless steel autoclave, 2.52 g (20.0 mmols) of melamine, 26.0 mg (0.1 mmol) of ruthenium trichloride, 2,101.0 mg (0.5 mmols) of tributylphosphine and 30 milliliters of 1-butanol were charged under a nitrogen atmosphere. The reaction mixture was heated and reacted at 230° C. under a nitrogen atmosphere (initial pressure was 5 kg/cm$^2$) for 2 hours.

After the completion of the reaction, the resulting crude reaction product was analyzed by HPLC under the above-mentioned first method. As a result, the conversion ratio of the starting melamine was 16.0%. Further, the crude mentioned first method. Consequently, 2-n-butylamino-4,6-diamino-1,3,5-triazine was formed with selectivity of 98.0% in a yield of 15.7% (based on the starting melamine).

EXAMPLE 9

Into a 100-mL stainless steel autoclave, 5.04 g (40.0 mmols) of melamine, 127.8 mg (0.2 mmol) of triruthenium dodecacarbonyl and 50 mililiters of 1-butanol were charged under nitrogen atomosphere. The reaction mixture was heated and reacted at 210° C. under a hydrogen/carbon monoxide (1/1 ratio) mixed gas (initial pressure was 80 kg/cm$^2$) for 10 hours.

After the completion of the reaction, the resulting crude reaction product was analyzed by HPLC under the above-mentioned first method. As a result, the conversion ratio of the starting melamine was 93.5%. Further, the crude reaction product was analyzed by HPLC under the above-mentioned first method. Consequently, the following products were obtained in the following yields (based on the starting melamine).

2-n-butylamino-4,6-diamino-1,3,5-triazine 12.5%

2,4-bis(n-butylamino)-6-amino-1,3,5-triazine 19.8%

2,4,6-tris(n-butylamino)-1,3,5-triazine 46.5%

2-di-n-butylamino-4,6-bis(n-butylamino)-1,3,5-triazine 11.6%

2,4-bis(di-n-butylamino)-6-n-butylamino-1,3,5-triazine 1.8%

After 1-butanol and water were distilled off from the crude reaction product, toluene was added to the residue. The insoluble portion was separated through filtration. As a result, 2-n-butylamino-4,6-diamino-1,3,5-triazine in a yield of 10.8% (based on the starting melamine) and 6.3% of the starting melamine were obtained.

EXAMPLE 10

Into a 100-mL stainless steel autoclave, 5.04 g (40.0 mmols) of melamine, 52.0 mg (0.2 mmol) of ruthenium chloride hydrate, 404.0 mg (1.0 mmol) of triphenylmethylphosphonium iodide and 50 milliliters of 1-butanol were charged under a nitrogen atmosphere. The reaction mixture was heated and reacted at 250° C. under a nitrogen atmosphere (initial pressure was 30 kg/cm$^2$) for 10 hours.

After the completion of the reaction, the resulting crude reaction product was analyzed by HPLC under the above-mention first method. As a result, the conversion ratio of the starting melamine was 42.3%. Further, the crude reaction product was analyzed by HLPC under the above-mentioned first method. Consequently, the following products were obtained in the following yields (based on the starting melamine).

2-n-butylamino-4,6-diamino-1,3,5-triazine 6.9%

2,4-bis(n-butylamino)-6-amino-1,3,5-triazine 15.7%

2,4,6-tris(n-butylamino)-1,3,5-triazine 14.4%

2-di-n-butylamino-4,6-bis(n-butylamino)-1,3,5-triazine 2.2%

After 1-butanol and water were distilled off from the crude reaction product, toluene was added to the residue. result, 2-n-butylamino-4,6-diamino-1,3,5-triazine in a yield of 4.8% (based on the starting melamine) and 55.5% of the starting melamine were obtained. The toluene solution was analyzed through HPLC. As a result, it was confirmed that a total amount of the other reaction product was extracted.

EXAMPLE 11

Into a 40-mL stainless steel autoclave, 1.87 g (10.0 mmols) of benzoguanamine, 26.0 mg (0.1 mmol) of ruthenium trichloride hydrate, 182.0 mg (0.5 mmol) of sodium diphenylphosphinobenzene-3-sulfonate and 20 milliliters of 1-butanol were charged under a nitrogen atmosphere. The reaction mixture was heated and reacted at 250° C. under a nitrogen atmosphere (initial pressure was 30 kg/cm$^2$) for 10 hours.

After the completion of the reaction, the resulting crude reaction product was analyzed by HLPC under the above-mentioned first method. As a result, the conversion ration of the starting triazine was 57.5%. Further, the crude reaction product was analyzed by HLPC under the above-mentioned first method. Consequently, the following products were obtained in the following yields (based on the starting triazine).

2-amino-4-n-butylamino-6-phenyl-1,3,5-triazine 48.0%

2,4-bis(n-butylamino)-6-phenyl-1,3,5-triazine 6.5%

After 1-butanol and water were distilled off from the crude reaction product, water was added to the residue, and the soluble portion was extracted and analyzed. As a result, 98.0% of the catalyst component was recovered.

EXAMPLE 12

Into a 40-mL stainless steel autoclave, 1.40 g (10.0 mmols) of 2-amino-4-methyl-6-methoxy-1,3,5-triazine, 95.8 mg (0.1 mmol) of dichlorotris(triphenylphosphine) ruthenium and 20 milliliters of 1-hexanol were charged under a nitrogen atmosphere. The reaction mixture was heated and reacted at 230° C. and under a nitrogen atmosphere (initial pressure was 5 kg/cm$^2$) for 20 hours.

After the completion of the reaction, the resulting crude reaction product was analyzed by HLPC under the above-mentioned first method. As a result, the conversion ratio of the starting triazine was 53.0%. Further, the crude reaction product was analyzed by HPLC under the above-mentioned first method. Consequently, 2-n-hexylamino-4-methyl-6-methoxy-1,3,5-triazine in a yield of 44.0% (based on the starting triazine).

EXAMPLE 13

Into a 100-mL stainless steel autoclave, 3.64 g (20.0 mmols) of 2-N-butylmelamine, 26.0 mg (0.1 mmol) of ruthenium trichloride, 182.0 mg (0.5 mmol) of sodium diphenylphosphinobenzene-3-sulfonate and 30 milliliters of 1-butanol were charged under a nitrogen atmosphere. The reaction mixture was heated and reacted at 230° C. under a nitrogen atmosphere (initial pressure was 5 kg/cm$^2$) for 1.5 hours.

After the completion of the reaction, the resulting crude reaction product was analyzed by HPLC under the above-mentioned first method. As a result, the conversion ratio of the starting triazine was 83.4%. Further, the crude reaction product was analyzed by HLPC under the above-mentioned first method. Consequently, the following conversion products were obtained in the following yields (based on the starting triazine).

2,4-bis(n-butylamino)-6-amino-1,3,5-triazine 36.7%

2,4,6-tris(n-butylamino)-1,3,5-triazine 41.5%

EXAMPLE 14

Into a 100-mL stainless steel autoclave, 4.76 g (20.0 mmols) of 2,4-bis(n-butylamino)-6-amino-1,3,5-triazine, 26.0 mg (0.1 mmol) of ruthenium trichloride, 182.0 mg (0.5 mmol) of sodium diphenylphosphinobenzene-3-sulfonate and 30 milliliters of 1-butanol were charged under a nitrogen atmosphere. The reaction mixture was heated and reacted at 230° C. under a nitrogen atmosphere (initial pressure was 5 kg/cm$^2$) for 0.5 hour.

After the completion of the reaction, the resulting crude reaction product was analyzed by HPLC by the above-mentioned first method. As a result, the conversion ratio of the starting triazine was 53.0%. Further, the crude reaction product was analyzed by HLPC under the above-mentioned first method. Consequently, the following products were obtained in the following yields (based on the starting triazine).

2,4,6-tris(n-butylamino)-1,3,5-triazine 36.5%

2-dibutylamino-4,6-bis(n-butylamino)-1,3,5-triazine 11.2% n-Butanol as a solvent and water formed were distilled off from the crude reaction mixture under reduced pressure, and 100 ml of toluene and 100 ml of water were added to the residue. The mixture was fully stirred, and the aqueous layer was then separated. The catalyst used was recovered in this aqueous layer. As a result of analysis, ruthenium derived from ruthenium chloride used was detected in the aqueous layer at a ratio of 99% calculated as ruthenium.

Further, sodium diphenylphosphinobenzene-3-sulfonate was detected at a ratio of 96% of the amount used and sodium diphenylphosphinobenzene-3-sulfonate oxide at a ratio of 2.5% off the amount used, respectively.

Still further, the residue obtained by concentrating the above-mentioned toluene layer was separated through silica-gel column chromatography [eluent—mixture of n-hexane and ethyl acetate at a ratio of 6:4 (v/v)]. Consequently, the starting material was recovered at a ratio of 43%, and 2,4,6-tris(n-butylamino)-1,3,5-triazine was separated in a yield of 33% and 2-dibutylamino-4,5-bis-(n-butylamino)-1,3,5-triazine in a yield of 8%, respectively.

EXAMPLE 15

Into a 100-mL stainless steel autoclave, 4.76 g (20.0 mmols) of 2-dibutylamino-4,6-diamino-1,3,5-triazine, 26.0 mg (0.1 mmol) of ruthenium trichloride hydrate, 182.0 mg (0.5 mmol) of sodium diphenylphosphinobenzene-3-sulfonate and 30 milliliters of 1-butanol were charged under a nitrogen atmosphere. The reaction mixture was heated and reacted at 230° C. under a nitrogen atmosphere (initial pressure was 5 kg/cm$^2$) for 3 hours.

After the completion of the reaction, the resulting crude reaction product was analyzed by HLPC under the above-mentioned first method. As a result, the conversion ratio of the starting triazine was 95.4%. Further, the crude reaction product was analyzed by HLPC under the above-mentioned first method. Consequently, the following products were obtained in the following yields (based on the starting triazine).

2-di-n-butylamino-4-n-butylamino-6-amino-1,3,5-triazine 37.0%

2-di-n-butyl-4,6-bis(n-butylamino)-1,3,5-triazine 33.2%

EXAMPLE 16

Into a 100-mL stainless steel autoclave, 3.64 g (20.0 mmols) of 2-N-butylmelamine, 63.9 mg (0.1 mmol) of trirutheniumdodecacarbonyl and 30 milliliters of 1-butanol were charged under a carbon monoxide atmosphere. The reaction mixture was heated and reacted at 230° C. for 2 hours under a carbon monoxide atmosphere.

After the completion of the reaction, the resulting crude reaction product was analyzed by HLPC under the above-mentioned first method. As a result, the conversion ratio of the starting triazine was 91.2%. Further, the crude reaction product was analyzed by HLPC under the above-mentioned first method. Consequently, the following products were obtained in the following yields (based on the starting triazine).

2,4-bis(n-butylamino)-6-amino-1,3,5-triazine 35.8%

2,4,6-tris(n-butylamino)-1,3,5-triazine 32.5%

EXAMPLE 17

Into a 100-mL stainless steel autoclave, 3.64 g (20.0 mmols) of 2-diethylamino-4,6-diamino-1,3,5-triazine, 26.0 mg (0.1 mmol) of ruthenium trichloride, 182.0 mg (0.5 mmol) of sodium diphenylphosphinobenzene-3-sulfonate and 30 milliliters of 1-butanol were charged under a nitrogen at 230° C. under a nitrogen atmosphere (initial pressure was atmosphere. The reaction mixture was heated and reacted 5 kg/cm$^2$) for 2 hours.

After the completion of the reaction, the resulting crude reaction product was analyzed by HLPC under the above-mentioned first method. As a result, the conversion ratio of the starting triazine was 67.8%. Further, the crude reaction product was analyzed by HLPC under the above-mentioned first method. Consequently, the following products were obtained in the following yields (based on the starting triazine).

2-diethylamino-4-n-butylamino-6-amino-1,3,5-triazine 28.8%

2-diethylamino-4,6-bis(n-butylamino)-1,3,5-triazine 25.3%

EXAMPLE 18

Into a 100-mL stainless steel autoclave, 4.76 g (20.0 mmols) of 2,4-bis(n-butylamino)-6-amino-1,3,5-triazine, 26.0 mg (0.1 mmol) of ruthenium trichloride, 182.0 mg (0.5 mmol) of sodium diphenylphosphinobenzene-3-sulfonate and 30 milliliters of 1-butanol were charged under a nitrogen atmosphere. The reaction mixture was heated and reacted at 250° C. under a nitrogen atmosphere (initial pressure was 5 kg/cm$^2$) for 30 minutes.

After the completion of the reaction, the resulting crude reaction product was analyzed by HLPC under the above-mentioned first method. As a result, the conversion ratio of the starting triazine was 93.4%.

1-Butanol and water formed were distilled off from the crude reaction product, and toluene and water were added to the residue in amounts of 100 mL each to conduct the extraction. The thus-obtained aqueous layer was analyzed, and it was found that 97.5% of the catalyst component was recovered. After the toluene layer was concentrated, the products were separated by silica-gel column chromatography (eluent—mixture of ethyl acetate and n-hexane =1 : 1). As a result, 2,4,6-tris(n-butylamino)-1,3,5-triazine was obtained in a yield of 63.2% and 2-dibutylamino-4,6-bis(n-butylamino)-1,3,5-triazine in a yield of 8.8%, respectively.

EXAMPLE 19

Into a 40-mL stainless steel autoclave, 1.96 g (10.0 mmols) of 2-morpholino-4,6-diamino-1,3,5-triazine, 95.8 mg (0.1 mmol) of dichlorotris(triphenylphosphine)-ruthenium and 20 milliliters of 1-hexanol were charged under a nitrogen atmosphere. The reaction mixture was heated and reacted at 200° C. under a nitrogen atmosphere (initial pressure was 5 kg/cm$^2$) for 20 hours.

After the completion of the reaction, the resulting crude reaction product was analyzed by HLPC under the above-mentioned first method. As a result, the conversion ratio of the starting triazine was 47.0%. Further, the crude reaction method. Consequently, 2-morpholino-4-n-butylamino-6-amino-1,3,5-triazine was obtained in a yield of 23.0% (based on the starting triazine).

INDUSTRIAL AVAILABILITY

According to the process of the present invention substituted 1,3,5-triazine derivatives which are a group of useful compounds that find wide acceptance in intermediates of fine chemicals such as agricultural chemicals, medications, dyestuffs, paints and the like and in resin materials and flame-retardant materials can be easily obtained from 1,3,5-triazines of formula (I) in high yields under relatively moderate reaction conditions.

The substituted 1,3,5-triazine derivatives which are alkylated by the method of the present invention are generally obtained in mixture form. However, these products can be separated in pure form by the method shown in Examples and be applied to various uses. In some uses (especially modified additives such as flame retardants and plasticizers for resins), the reaction mixtures can be used as such without being separated.

Further, many of the substituted triazines obtained by the reaction of the present invention have been relatively hard to produce so far, and are therefore interesting in terms of solubility in water or various organic solvents, stability at high temperatures, melting point, boiling point and basicity. Accordingly, these compounds are considered to find wider acceptance than before.

We claim:

1. A method for alkylation of melamine, which comprises reacting the melamine 1,3,5-triazine derivatives having at least one or more amino groups or mono-substituted amino groups with alcohols in the presence of at least one catalyst selected from the group consisting of iron, cobalt, ruthenium and rhodium.

2. A method for alkylation of melamine as claimed in claim 1, wherein the alcohols are alcohol derivatives represented by formula (II)

$$ROH \qquad (II)$$

wherein R represents a $C_{1-20}$ alkyl group, said alkyl group optionally substituted with a hydroxyl group, a trifluoromethyl group, a $C_{1-16}$ alkoxy group, a $C_{1-6}$ haloalkoxy group, a $C_{2-7}$ alkoxycarbonyl group or a phenyl group (said phenyl group is optionally substituted with a halogen atom, a $C_{1-6}$ alkyl group or a $C_{16}$ alkoxy group), or a $C_{2-20}$ alkenyl group, said alkenyl group is optionally substituted with a trifluoromethyl group, a $C_{1-6}$ alkoxy group, a $C_{1-6}$ haloalkoxy group, a $C_{2-7}$ alkoxycarbonyl group or a phenyl group (said phenyl group is optionally substituted with a halogen atom, a $C_{16}$ alkyl group or a $C_{1-1-6}$ alkoxy group).

3. A method for alkylation of melamine as claimed in claim 2, wherein R of the alcohol derivatives represented by the formula (II) represents a $C^{1-20}$ alkyl group (said alkyl group is optionally substituted with a $C_{1-6}$ alkoxy group or a phenyl group) or a $C_{2-20}$ alkenyl group (said alkenyl group is optionally substituted with a $C_{1-6}$ alkoxy group or a phenyl group).

4. A method for alkylation of melamine as claimed in claim 3, wherein R of the alcohol derivatives represented by the formula (II) represents a $C_{1-10}$ alkyl group (said alkyl group is optionally substituted with a $C_{1-6}$ alkoxy group or a phenyl group).

5. A method for alkylation of melamine as claimed in claim 1, wherein the catalyst is at least one catalyst selected from the group consisting of ruthenium and rhodium.

6. A method for alkylation of melamine as claimed in claim 5, wherein the catalysts are complex catalysts.

7. A method for alkylation of melamine as claimed in claim 6, wherein the complex catalysts are added with a ligand of tertiary phospines.

8. A method for alkylation of melamine as claimed in claim 5, wherein the catalysts are elements-carried catalysts.

9. A method for alkylation of melamine as claimed in claim 8, wherein carriers of the elements-carried catalysts are selected from the group consisting of silica, alumina and carbon.

10. A method for alkylation of melamine claimed in claim 7, wherein the catalysts are elements-carried catalysts.

11. A method for alkylation of melamine as claimed in claim 10, wherein carries of the elements-carried catalysts are silica, alumina and carbon.

12. A method for alkylation of melamine as claimed in claim 1, wherein the catalysts are complex catalysts.

13. A method for alkylation of melamine as claimed in claim 12, wherein the complex catalysts are added with a ligand of tertiary phosphines.

14. A method for alkylation of melamine as claimed in claim 1, wherein the catalysts are elements-carried catalysts.

15. A method for alkylation of melamine as claimed in claim 14, wherein carriers of the elements-carried catalysts are selected from the group consisting of silica, alumina and carbon.

16. A method of alkylation of melamine claimed in claim 13, wherein the catalysts are selected from the group consisting of elements-carried catalysts.

17. A method for alkylation of melamine as claimed in claim 16, wherein carriers of the elements-carried catalysts are selected from the group consisting of silica, alumina and carbon.

* * * * *